(12) United States Patent
Park et al.

(10) Patent No.: US 11,020,253 B2
(45) Date of Patent: Jun. 1, 2021

(54) MULTI-HOLE STENT FOR DIGESTIVE ORGANS

(71) Applicant: M.I.TECH CO., LTD., Pyeongtaek-si (KR)

(72) Inventors: Hun Kuk Park, Pyeongtaek-si (KR); Bong Seok Jang, Osan-si (KR); Ho Yun, Asan-si (KR); Jong Pil Moon, Gunpo-si (KR); So Mi Ji, Osan-si (KR); Kyoung Sub Shin, Gunpo-si (KR); Makoto Kobayashi, Yokkaichi Mie (JP)

(73) Assignee: M.I. TECH CO., LTD., Pyeongtaek-si (KR)

( * ) Notice: Subject to any disclaimer, the term of this patent is extended or adjusted under 35 U.S.C. 154(b) by 192 days.

(21) Appl. No.: 16/311,050

(22) PCT Filed: Jun. 23, 2016

(86) PCT No.: PCT/KR2016/006672
§ 371 (c)(1),
(2) Date: Dec. 18, 2018

(87) PCT Pub. No.: WO2017/222090
PCT Pub. Date: Dec. 28, 2017

(65) Prior Publication Data
US 2019/0175374 A1  Jun. 13, 2019

(51) Int. Cl.
*A61F 2/90* (2013.01)
*A61F 2/06* (2013.01)
*A61F 2/07* (2013.01)
*A61F 2/91* (2013.01)
(Continued)

(52) U.S. Cl.
CPC ................ *A61F 2/90* (2013.01); *A61F 2/06* (2013.01); *A61F 2/07* (2013.01); *A61F 2/852* (2013.01);
(Continued)

(58) Field of Classification Search
CPC ...... A61F 2/04–2/042; A61F 2002/045; A61F 2002/048; A61F 2002/047;
(Continued)

(56) References Cited

U.S. PATENT DOCUMENTS 5,195,984 A    3/1993  Schatz ........................ 606/195
5,735,892 A *  4/1998  Myers ...................... A61F 2/07
                                                        606/198

(Continued)

FOREIGN PATENT DOCUMENTS

CN           2899742 Y       5/2007
DE    10 2010 018 539 A1    11/2011
(Continued)

OTHER PUBLICATIONS

Japanese Office Action issued to Japanese Application No. 2018-560971.
(Continued)

*Primary Examiner* — Paul B Prebilic
(74) *Attorney, Agent, or Firm* — Stein IP, LLC (57) ABSTRACT

The present invention relates to a multi-hole stent for digestive organs, the multi-hole stent including: a body configured to form a plurality of cells through the intersection of wires and to be provided in a hollow cylindrical shape; and a film configured to be installed in contact with the inner surface of the body; wherein one or more discharge holes are formed in the film. The multi-hole stent for digestive organs is placed in a stenotic region in a biliary track, and can thus secure a discharge path by restoring a narrowed diameter. Furthermore, the film is installed on the inner surface of the body, and can thus prevent the entry of a lesion into the stent and re-stenosis attributable to the growth of the lesion and can thus provide discharge paths for (Continued)

body fluids generated from side branches through the discharge holes formed in the film.

3 Claims, 8 Drawing Sheets (51) Int. Cl.
*A61F 2/852* (2013.01)
*A61F 2/04* (2013.01)
(52) U.S. Cl.
CPC .......... *A61F 2/91* (2013.01); *A61F 2002/041* (2013.01); *A61F 2002/075* (2013.01); *A61F 2230/006* (2013.01); *A61F 2230/0069* (2013.01)
(58) Field of Classification Search
CPC ........ A61F 2/07–2002/075; A61F 2/88; A61F 2/885; A61F 2/90–2/915; A61F 2210/0076; A61F 2230/0069; A61F 2250/0023; A61F 2250/0024; A61F 2250/0039; A61F 2250/0051; A61F 2/06; A61F 2230/006
See application file for complete search history.

(56) References Cited

U.S. PATENT DOCUMENTS

| | | | | |
|---|---|---|---|---|
| 7,854,760 | B2* | 12/2010 | Molaei | A61F 2/07 623/1.38 |
| 10,349,944 | B2* | 7/2019 | Han | A61F 2/90 |
| 2006/0036311 | A1 | 2/2006 | Nakayama et al. | 623/1.15 |
| 2006/0217799 | A1* | 9/2006 | Mailander | A61F 2/915 623/1.44 |
| 2007/0100437 | A1 | 5/2007 | Welborn et al. | 623/1.44 |
| 2007/0275156 | A1 | 11/2007 | Tanaka et al. | 427/2.24 |
| 2009/0306759 | A1 | 12/2009 | Richter | 623/1.11 |
| 2010/0161033 | A1* | 6/2010 | Jantzen | A61F 2/07 623/1.16 |
| 2011/0319980 | A1* | 12/2011 | Ryan | A61F 2/07 623/1.16 |
| 2013/0018452 | A1 | 1/2013 | Weitzner et al. | 623/1.15 |
| 2013/0261732 | A1 | 10/2013 | Perkins et al. | 623/1.15 |
| 2014/0107763 | A1 | 4/2014 | Layne et al. | 623/1.16 |
| 2014/0277573 | A1 | 9/2014 | Gill et al. | 623/23.68 |
| 2014/0358221 | A1 | 12/2014 | Ho et al. | 623/1.35 |

FOREIGN PATENT DOCUMENTS

| | | |
|---|---|---|
| KR | 10-2002-0080024 A | 10/2002 |
| KR | 10-2016-0081184 A | 7/2016 |

OTHER PUBLICATIONS

International Search Report dated Mar. 15, 2017, issued to International Application No. PCT/KR2016/006672.
Extended European Search Report dated Nov. 8, 2019, issued to European Application No. 16906366.6.

* cited by examiner

-- Prior Art --

FIG. 4(b)

-- Prior Art --

FIG. 4(c)

-- Prior Art --

FIG. 5(a)

-- Prior Art --

MULTI-HOLE STENT FOR DIGESTIVE ORGANS

CROSS-REFERENCE TO RELATED APPLICATIONS

This application is a national stage of International Application No. PCT/KR2016/006672, filed Jun. 23, 2016, the disclosure of which is incorporated herein by reference.

TECHNICAL FIELD

The present invention relates to a stent for digestive organs.

BACKGROUND ART

Generally, stents are used for the purpose of expanding stenotic regions. Stents are formed in accordance with usages based on the sizes and characteristics of various types of organs and lumens where the stents will be placed, and environments. Stents are provided to overcome the blocking or obstruction of flows of material attributable to the stenosis of lumens and to maintain the sufficient diameters of the lumens for long periods.

Each of such stents includes a body composed of wires and configured to form a basic skeleton, and may further include a film or coating configured to cover the body in order to prevent material from moving from the side of the stent to the inside of the stent in the inside or outside of the corresponding body.

The film structure that is provided to prevent various types of body materials from entering the inside of the stent through the cell structure of the stent provided in a specific pattern through the bending of the wires constituting the body and to more effectively restore a lumen narrowed by a lesion region generally has a closed structure all over the surface of the film in order to achieve the above-described purpose.

A prior art document regarding such a stent equipped with a film or coating structure configured to prevent materials from moving from a side surface by covering the outer or inner surface of a body formed by wires includes Korean Patent No. 10-0448329 entitled "Stent for Expansion of Lumen" (hereafter referred to as 'prior art').

First, in the case of a wire-only stent without a film structure, the stent is placed in a stenotic region of a lumen, and continues to expand the stenotic region during an initial period. However, as a lesion, such as a malignant tumor, grows through the spaces of cells opened and formed at the intersections of wires of the stent placed in the stenotic region, re-stenosis and a phenomenon in which the locations where the wires have been installed are changed or the structure of the wires is deformed occur frequently when a predetermined period has elapsed after the placement of the stent.

Furthermore, in the case of a conventional stent having a closed-type film structure as in the prior art, entry into the stent attributable to the growth of a lesion is blocked. However, a problem occurs during a process in which a stent is placed in order to restore a stenotic region that has occurred in one of branch lumens in a bodily organ having a plurality of lumens branched off from a main lumen, such as a Y-shape bodily organ.

More specifically, a film structure on the outer surface of the stent placed in one of the branch lumens may obstruct various body materials, such as body fluids and digestive fluids, which may be provided by the other branch lumens, and thus the congestion of the corresponding materials may occur, with the result that a problem may arise in that occlusion occurs in the movement paths of the other branch lumens.

DISCLOSURE

Technical Problem

The present invention has been conceived to overcome the above-described problems, and an object of the present invention is to provide a stent having technology by which the stent is placed in a lumen having a branched structure and expands a stenotic region attributable to a lesion having occurred in one of branch lumens, thereby restoring the diameter of the lumen and also securing discharge paths for body fluids generated from the other branch lumens.

Furthermore, another object of the present invention is to provide a stent having technology by which the degree of the prevention of separation attributable to a lesion can be improved in connection with the growth of the lesion having occurred in a lumen in which the stent has been placed and the removal of the lesion can be easily and efficiently performed.

Technical Solution

In order to accomplish the above objects, the present invention provides a multi-hole stent for digestive organs, the multi-hole stent including: a body configured to form a plurality of cells through the intersection of wires and to be provided in a hollow cylindrical shape; and a film configured to be installed in contact with the inner surface of the body; wherein one or more discharge holes are formed in the film.

In this case, the discharge holes are formed in a smaller size than the cells formed in the body.

Furthermore, the discharge holes are formed to be located within the cells formed in the body when the film is installed the inner surface of the body.

Additionally, the body includes a body part configured to be formed in a hollow cylindrical shape, and upper and lower head parts configured to be formed on both ends of the body part to have a larger diameter than the body part; the film includes a body film part configured to be located on the inner surface of the body part, and upper and lower head film parts configured to be located on the inner surfaces of the upper and lower head parts; and the discharge holes include one or more discharge holes formed in the body film part.

Advantageous Effects

According to the present invention, the following effects are achieved:

First, the stent is placed in a stenotic region of a lumen of a digestive system and restores a narrowed diameter, and thus paths for the discharge of materials through the corresponding lumen can be secured.

Second, the film is installed on the inner surface of the body, and thus entry into the inside of the stent and re-stenosis attributable to the growth of a lesion, such as a malignant tumor, of a stenotic region can be prevented.

Third, even when the stent is placed in one of branch lumens having a Y-shaped structure, discharge paths for body fluids generated from the other branch lumen can be provided through the plurality of discharge holes formed in the film.

Fourth, when the placed multi-hole stent for digestive organs is removed, the phase of the plurality of discharge holes formed in the film is moved along with the stent in the direction in which the stent is removed, and thus a lesion entering and protruding through the plurality of discharge holes can be easily removed during a process of removing the stent.

Fifth, when a lesion, such as a malignant tumor, having occurred in a stenotic region is removed and extracted, a lesion entering and protruding through the plurality of discharge holes formed in the film can be easily removed by inserting a removal means into the stent and then performing treatment.

Sixth, the predetermined portions of a stenotic region are inserted through the plurality of discharge holes formed in the film, and thus stronger fastening force for the prevention of the movement of the overall placed stent can be provided.

MODE FOR INVENTION

Preferred embodiments of the present invention will be described in greater detail with reference to the accompanying drawings, but descriptions of well-known technical parts will be omitted or abridged for brevity of description.

<Description of the Components and Operation of a Multi-Hole Stent for Digestive Organs>

Figure 1:
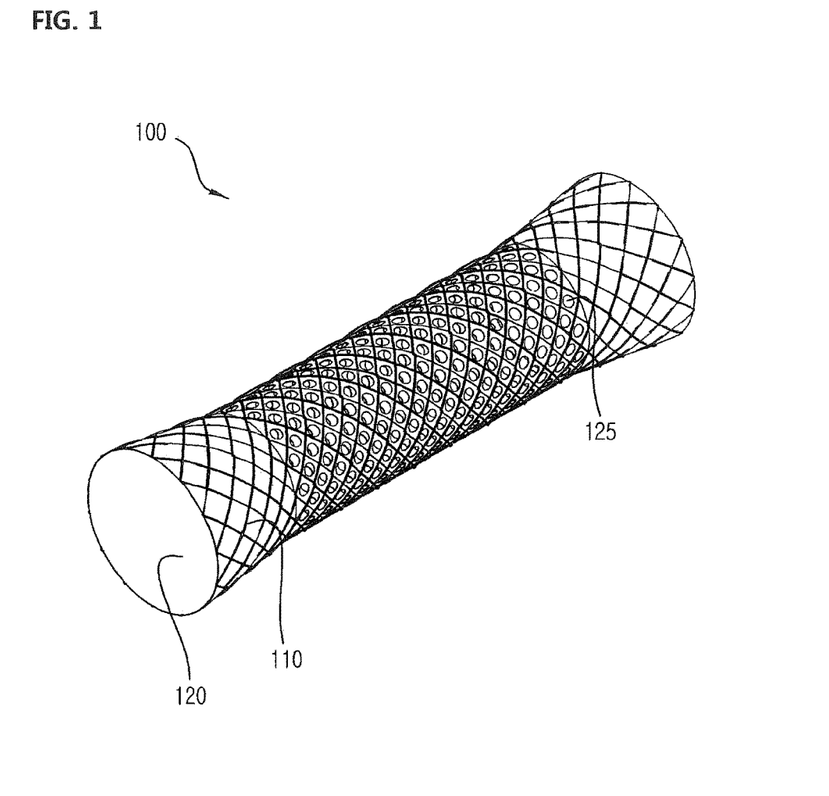
FIG. 1 is a perspective view showing a multi-hole stent for digestive organs according to the present invention.
Figure 2:
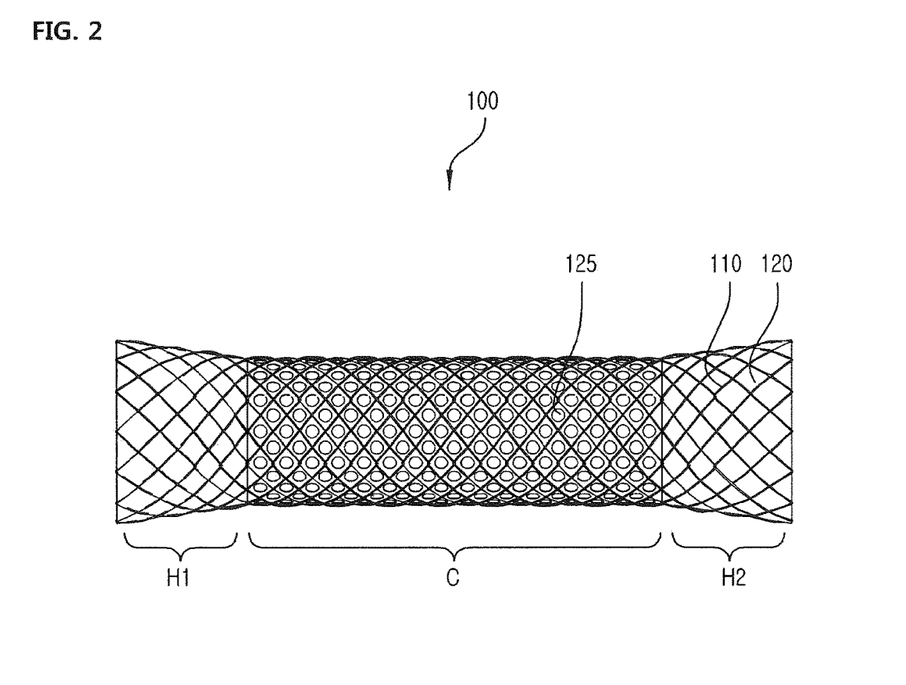
FIG. 2 is a front surface showing the multi-hole stent for digestive organs according to the present invention.
Figure 3:
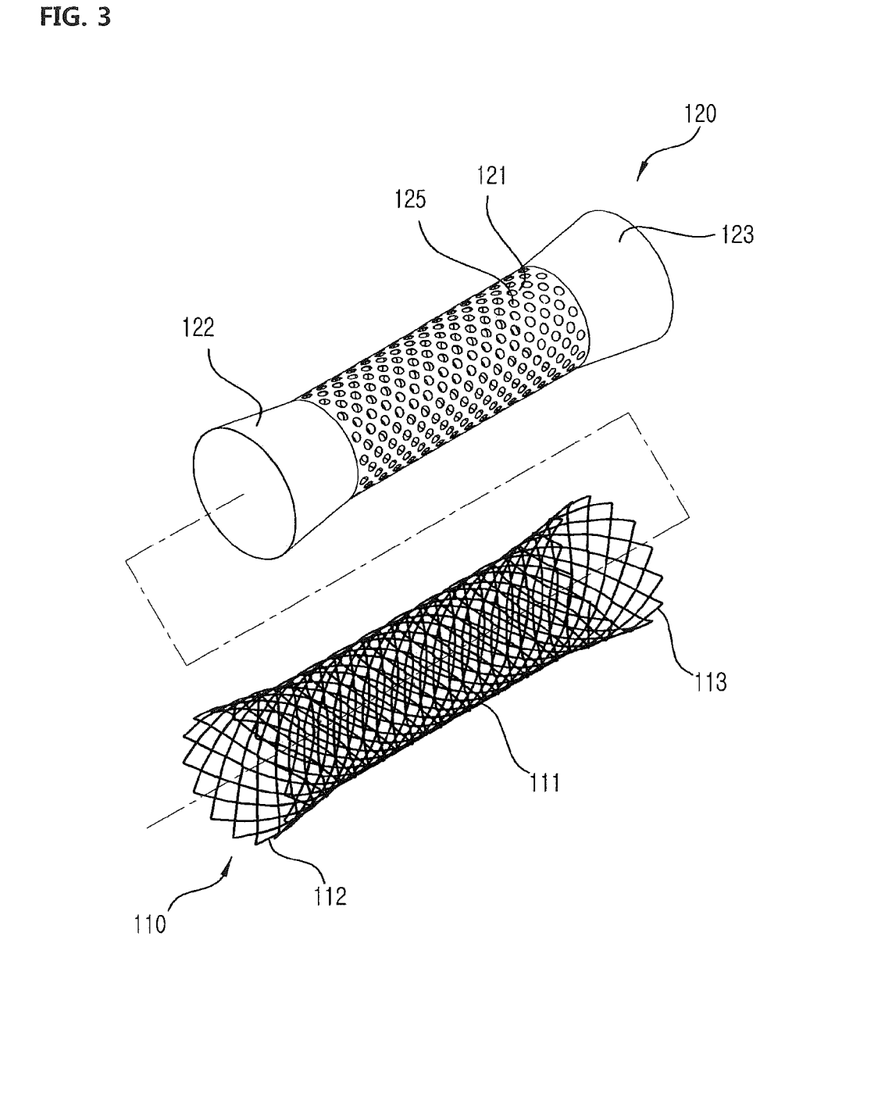
FIG. 3 is an exploded perspective view showing the multi-hole stent for digestive organs according to the present invention.

Referring to FIGS. 1 to 3, a multi-hole stent 100 for digestive organs according to the present invention includes: a body 110; and a film 120.

The body 110 forms a plurality of cells through the intersection of wires, and is provided in a hollow cylindrical shape. In this case, as shown in FIG. 3, more specifically, the body 110 is provided to include: a body part 111 configured to be located at the center of the body 110, and provided in a hollow cylindrical shape; an upper head part 112 configured to extend from one end of the body part 111 and to have a larger diameter than the body part 111; and a lower head part 113 configured to extend from the other end of the body part 111 and to have a larger diameter than the body part 111.

The shape of the body 110 and the structure of the plurality of cells opened and formed by the intersection of the wires constituting the body are not limited to specific forms, but may be provided in various manners.

The film 120 is installed in contact with the inner surface of the body 110, and one or more discharge holes 125 are formed in the film 120.

In this case, although the material of the film may be selected from among polytetrafluoroethylene (PTFE), silicone, polyurethane, polyester, polypropylene, polyethylene, polyolefin, high density polyethylene (HDPE), and expanded-polytetrafluoroethylene (ePTFE), it may be selected within the range of well-known materials, used for films, without a particular limitation.

In this case, as shown in FIG. 3, in order to correspond to the configuration of the body 110, the film 120 is also formed to include: a body film part 121 configured to be located on the inner surface of the body part 111; and upper and lower head film parts 122 and 123 configured to be located on the inner surfaces of the upper and lower head parts 112 and 113.

Furthermore, the discharge holes 125 are provided in the form of circular holes having a smaller diameter than the plurality of cells formed in the body 110, as shown in FIG. 2. When the film 120 is installed on the inner surface of the body 110, the discharge holes 125 are formed to be located to correspond to the internal spaces of the cells, as shown in FIG. 2.

In this case, the locations at which the discharge holes 125 are formed in the film 120 may be formed in various manners within a structural range provided so that the size of the discharges holes 125 can be smaller than that of the cells provided in the body 110 and the discharges holes 125 can be located within the cells. More specifically, one or more discharge holes 125 are preferably formed in the body film part 121.

Figure 6:
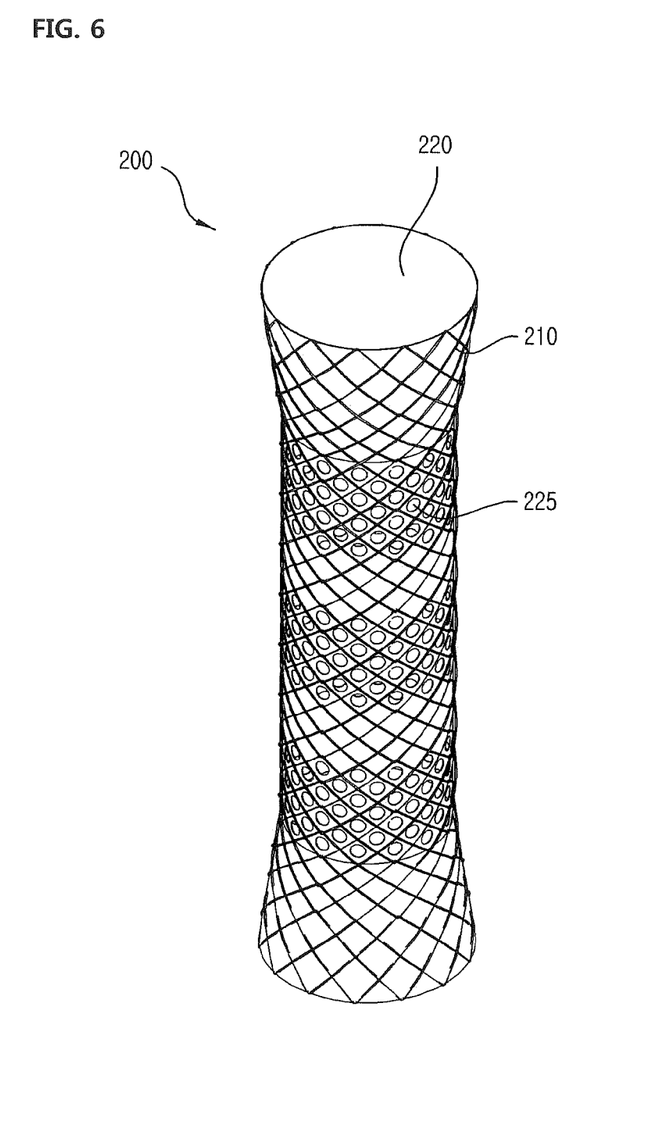
FIGS. 6 to 8 are perspective views showing various embodiments of multi-hole stents for digestive organs according to the present invention.
Figure 7:
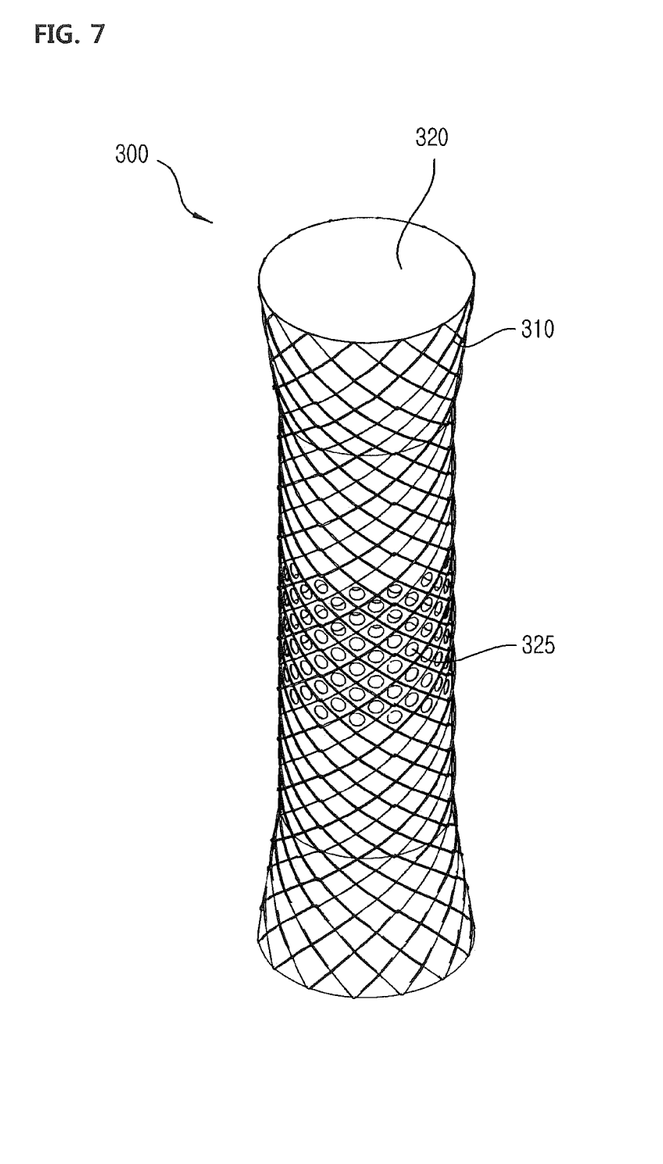
Figure 8:
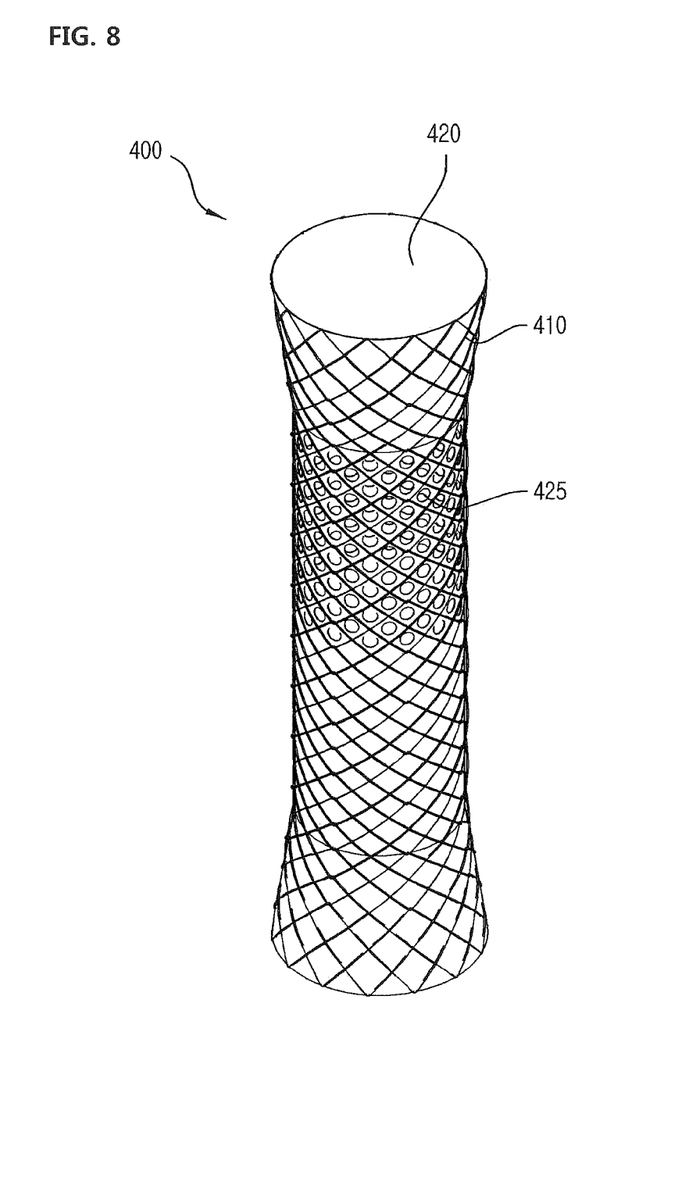

Multi-hole stents for digestive organs 100, 200, 300 and 400 each having discharge holes 125 provided in a body film part 121 in various forms of formation over all or part of the body film part 121 may be provided as various embodiments, as shown in FIGS. 6 to 8.

In other words, although the locations where the discharge holes 125 are formed may be formed in the body film part 121 in various directions according to various embodiments, the size of the discharge holes 125 is preferably smaller than that of the cells formed in the body 110, and the locations where the discharge holes 125 are disposed when the film 120 is combined with the body 110 are preferably placed within the cells.

For example, as shown in FIG. 6, in a multi-hole stent for digestive organs 200 according to a second embodiment, a film 220 is configured such that one or more discharge holes 225 having a smaller size than cells are located within the cells that form predetermined columns formed in the central circumferential direction of a body film part 221 and predetermined columns formed in the circumferential directions of both ends of the body film part 221.

The discharge holes 125 provided in the film 120 in various structures of formation perform various functions compared to conventional stents 20 and 30 for digestive organs, and allow the stent to act in a more improved manner when stent insertion into a biliary track is performed.

Figure 4A:
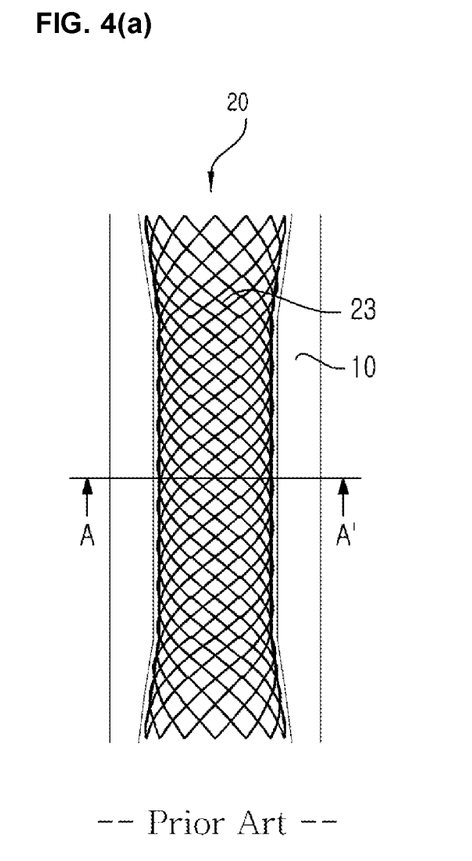
FIG. 4 shows the state of the growth of a stenotic region attributable to the placement of a conventional wire-type stent in a stenotic region.
Figure 4B:
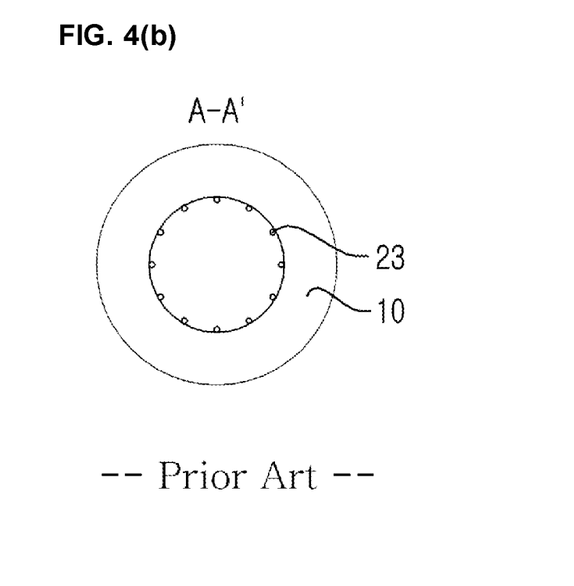
Figure 4C:
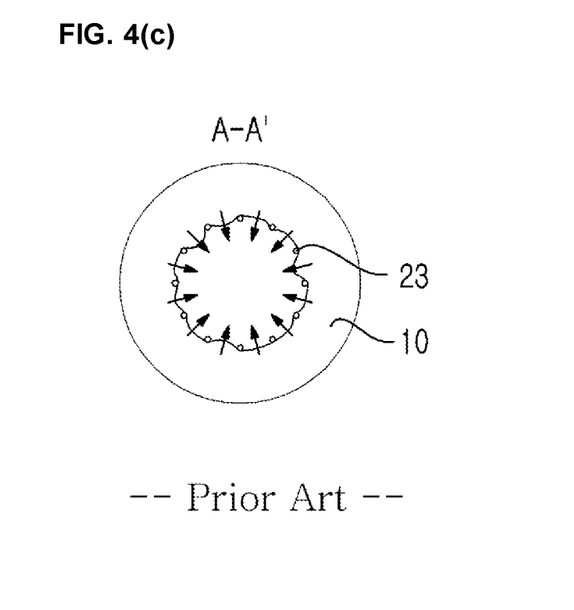

A description will be given in greater detail in comparison with the conventional wire-type stent 20 shown in FIG. 4. In the case of the conventional wire-type stent 20, wires 23 are formed to maintain a predetermined expanded diameter, as shown in FIG. 4(b) after the wires 23 have been placed in a stenotic region 10 and has performed expansion, as shown in FIG. 4(a). However, in this case, over the passage of time, the stenotic region 10 where a lesion, such as a malignant tumor, has occurred grows gradually, enters the inside of the stent through spaces between the cells of the stent, and finally covers the wires 23, thereby causing re-stenosis, as shown in FIG. 4(c).

Figure 5A:
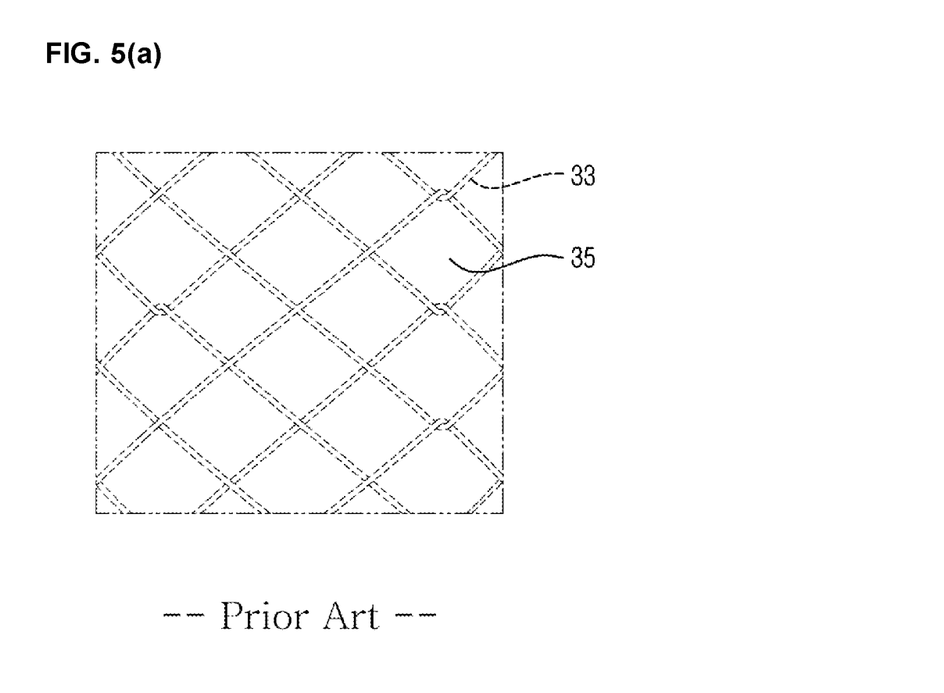
FIG. 5 shows the states of the growth of a stenotic region attributable to the placement of a conventional cover-type stent in the stenotic region and the placement of a multi-hole stent for digestive organs according to the present invention in the stenotic region.

Thereafter, in order to block the entry of a lesion, such as a malignant tumor, in the stenotic region 10 into the inside of the stent and prevent re-stenosis, the cover-type stent 30 has been developed by installing a cover-type film 35 in the conventional wire-type stent 20. However, the conventional cover-type stent 30 is problematic in that discharge paths for body fluids and digestive fluids, such as bile, that can be provided in a lateral direction are blocked by unconditional occlusion, as shown in FIG. 5(a).

Figure 5B:
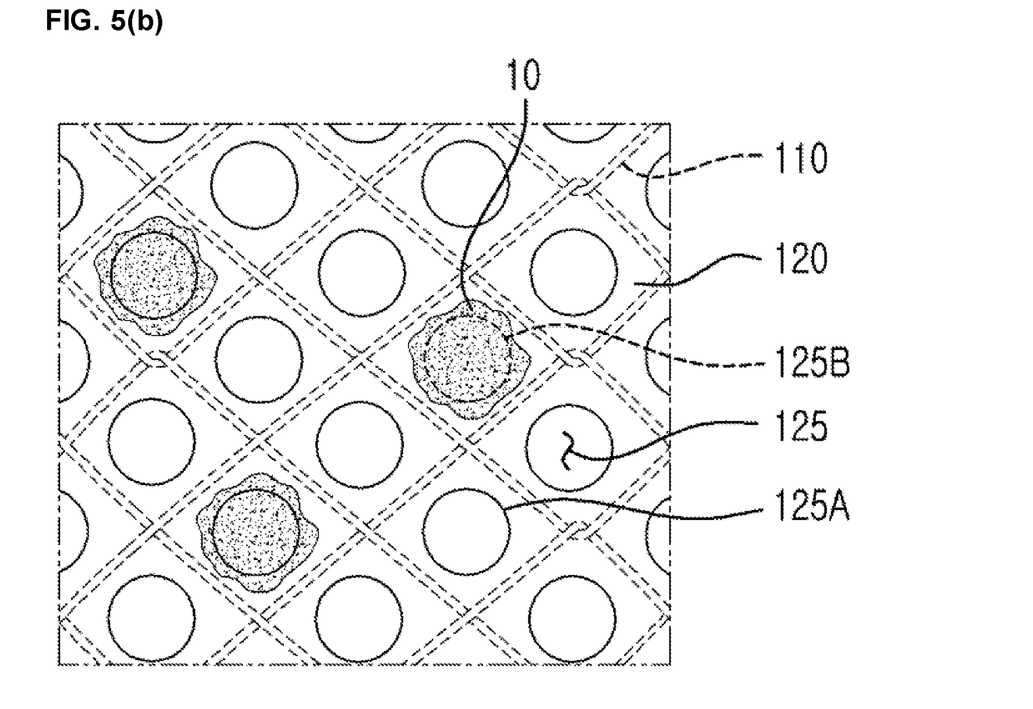

Therefore, the multi-hole stent 100 for digestive organs according to the invention of the present application is configured such that the discharge holes 125 are formed in the film 120 in a predetermined pattern and expand the stenotic region of a stenotic lumen among the branch lumens of a Y-shaped bodily organ, as shown in FIG. 5(b). Accordingly, the discharge paths of the corresponding lumen can be secured, re-stenosis can be prevented by reducing the excessive entry of a lesion, and discharge paths for body fluids generated from the other branch lumen excluding the stenotic lumen and a digestive fluid, such as bile, provided in a lateral direction can be also secured.

Furthermore, as shown in FIG. 5(b), among the discharge holes 125 formed in the film 120, discharge holes 125A through which a lesion has not entered the inside of the stent may be used as spaces through which body fluids can be discharged from lumens corresponding to side branches, and discharge holes 125B which have been entered by a lesion, such as a malignant tumor, function as auxiliary spaces which eliminate the entered lesion.

For example, during a process of removing the stent via a pulling member when a predetermined period has elapsed after the placement of the multi-hole stent 100 for digestive organs, a lesion region having grown and entered the stent through the discharge holes 125B and foreign materials generated from the lesion region are influenced by the phase of the discharge holes 125B moved in association with the pulling of the stent, and can be thus easily removed along with the multi-hole stent 100 for digestive organs.

Furthermore, the discharge holes 125B of the multi-hole stent 100 for digestive organs fasten and secure a surgical site in order to facilitate the cutting and removal of a lesion region, having grown and entered the stent, via a surgical tumor removal means that is introduced into the stent, thereby assisting with removal surgery.

Moreover, the discharge holes 125B that have been entered by part of a lesion, such as a malignant tumor, assist in providing fastening force in the stenotic region 10 for the placed multi-hole stent 100 for digestive organs by means of the part of the lesion in the stenotic region 10, which has been inserted into the stent, thereby implementing improved movement prevention.

The embodiments disclosed in the present invention are not intended to limit the technical spirit of the present invention, but are intended to describe it. The scope of the technical spirit of the present invention is not limited by these embodiments. The range of protection of the present invention should be interpreted based on the attached claims, and all technical spirits falling with a range equivalent to the attached claims should be also interpreted as being included in the range of rights of the present invention.

DESCRIPTION OF REFERENCE SYMBOLS

10: stenotic region
20: conventional wire-type stent
23: wire of a conventional wire-type stent
30: conventional cover-type stent
33: wire of a conventional cover-type stent
35: film of the conventional cover-type stent
100, 200, 300, 400: multi-hole stent for digestive organs
110: body
111: body part
112: upper head part
113: lower head part
120: film
121: body film part
122: upper head film part
123: lower head film part
125: discharge hole

The invention claimed is:

1. A multi-hole stent for digestive organs, the multi-hole stent comprising:
a body that includes a plurality of cells defined by intersections of wires and having a hollow cylindrical shape; and
a separate film having a corresponding hollow cylindrical shape that is configured to be placed into detachable contact with an inner surface of the body,
wherein:
the body includes a body part formed in a hollow cylindrical shape, and upper and lower head parts formed on both ends of the body part each having a larger diameter than the body part;
the film includes a body film part configured to be located on an inner surface of the body part, and upper and lower head film parts configured to be located on inner surfaces of the upper and lower head parts; and
a plurality of discharge holes are formed in the body film part, the plurality of discharge holes are arranged to be located within the cells formed in the body when the film is installed on the inner surface of the body,
the plurality of discharge holes are smaller in size than the cells formed in the body,
one or more of the plurality of discharge holes are formed in a portion of the body film part that is structured to come into contact with a lesion of a lumen in which the stent is placed so that the lesion can enter the discharge holes through growth,
no discharge holes are formed in the upper and lower head film parts, and
the stent is removable after the placement of the stent into the digestive organ such that any lesion entering the discharge holes is removed along with the stent when removing the stent.

2. The multi-hole stent of claim 1, wherein at least one of the cells formed in the body corresponds only to a single discharge hole of the plurality of discharge holes formed in the body film part when the film is installed on the inner surface of the body.

3. The multi-hole stent of claim 2, wherein the at least one of the cells is each of the cells formed in the body.

* * * * *